(12) United States Patent
Von Hollen et al.

(10) Patent No.: US 9,352,107 B2
(45) Date of Patent: May 31, 2016

(54) RESPIRATORY DRUG DELIVERY APPARATUS INCLUDING A FEEDBACK AND COMPLIANCE DEVICE

(75) Inventors: Dirk Ernest Von Hollen, Clark, NJ (US); Jonathan Stanley Harold Denyer, Chichester (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 366 days.

(21) Appl. No.: 13/520,970

(22) PCT Filed: Dec. 7, 2010

(86) PCT No.: PCT/IB2010/055642
§ 371 (c)(1),
(2), (4) Date: Jul. 6, 2012

(87) PCT Pub. No.: WO2011/083377
PCT Pub. Date: Jul. 14, 2011

(65) Prior Publication Data
US 2013/0008436 A1   Jan. 10, 2013

Related U.S. Application Data

(60) Provisional application No. 61/293,020, filed on Jan. 7, 2010.

(51) Int. Cl.
*A61M 15/00* (2006.01)
*A61M 11/00* (2006.01)
(Continued)

(52) U.S. Cl.
CPC ....... *A61M 15/0086* (2013.01); *A61M 15/0005* (2014.02); *A61M 15/009* (2013.01);
(Continued)

(58) Field of Classification Search
CPC ... A61M 11/00; A61M 11/08; A61M 11/042; A61M 11/006; A61M 15/00; A61M 15/0001; A61M 15/0021; A61M 15/0018; A61M 15/0013; A61M 15/0065; A61M 15/0068; A61M 15/008; A61M 15/009; A61M 15/0091; A61M 15/0095; A61M 11/007; A61M 15/0005; A61M 15/0086; A61M 15/0016

USPC ............ 128/200.24, 200.14, 200.16, 200.21, 128/203.12, 203.15, 203.24, 204.14; 434/236, 238, 127

See application file for complete search history.

(56) References Cited

U.S. PATENT DOCUMENTS

| 4,470,412 A | 9/1984 | Nowacki et al. |
| 4,809,692 A | 3/1989 | Nowacki et al. |

(Continued)

FOREIGN PATENT DOCUMENTS

| EP | 0933092 A1 | 8/1999 |
| GB | 2406283 A | 3/2005 |

(Continued)

OTHER PUBLICATIONS

Laura T. Scarpaci et al; "Assessment of Hospice Nurses' Technique in the Use of Inhalers and Nebulizers:", Journal of Palliative Medicine, vol. 10, No. 3, 2007, pp. 665-676.

(Continued)

*Primary Examiner* — Valerie L Woodward
*Assistant Examiner* — Tu Vo
(74) *Attorney, Agent, or Firm* — Michael W. Haas

(57) ABSTRACT

A respiratory drug delivery apparatus (2) includes a medication storage and delivery device (8) having an outlet (30) and a feedback and compliance device (32) coupled thereto. The feedback and compliance device has an opening, and the outlet of the medication storage and delivery device is received through the opening. The feedback and compliance device includes: (i) one or more sensors (46, 52, 54, 56), each of the one or more sensors being structured to sense a parameter relating to use of the respiratory drug delivery apparatus without modifying or interfering with a flow of medication introduced by actuation of the medication storage and delivery device, (ii) one or more feedback devices (48, 50, 62), and (iii) a processing unit (42) programmed to cause the one or more feedback devices to provide feedback information to a patient (4) regarding use of the respiratory drug delivery apparatus based on an output of at least one of the one or more sensors.

33 Claims, 9 Drawing Sheets

(51) Int. Cl.
*A61M 11/08* (2006.01)
*A61M 16/00* (2006.01)

(52) U.S. Cl.
CPC ....... *A61M15/0016* (2014.02); *A61M 15/0018* (2014.02); *A61M 11/006* (2014.02); *A61M 11/007* (2014.02); *A61M 11/08* (2013.01); *A61M 2016/0021* (2013.01); *A61M 2016/0039* (2013.01); *A61M 2205/13* (2013.01); *A61M 2205/14* (2013.01); *A61M 2205/276* (2013.01); *A61M 2205/332* (2013.01); *A61M 2205/3306* (2013.01); *A61M 2205/3368* (2013.01); *A61M 2205/3375* (2013.01); *A61M 2205/43* (2013.01); *A61M 2205/44* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/8206* (2013.01)

(56) References Cited

U.S. PATENT DOCUMENTS

| | | | |
|---|---|---|---|
| 4,832,015 A | | 5/1989 | Nowacki et al. |
| 4,984,158 A | * | 1/1991 | Hillsman ................. 128/200.14 |
| 5,012,803 A | | 5/1991 | Foley et al. |
| 5,042,467 A | | 8/1991 | Foley |
| 5,167,506 A | * | 12/1992 | Kilis et al. .................... 434/262 |
| 5,331,953 A | * | 7/1994 | Andersson et al. ...... 128/200.14 |
| 5,333,106 A | | 7/1994 | Lanpher et al. |
| 5,363,842 A | * | 11/1994 | Mishelevich et al. .... 128/200.14 |
| 5,385,140 A | | 1/1995 | Smith |
| 5,385,549 A | | 1/1995 | Lampropoulos et al. |
| 5,394,866 A | | 3/1995 | Ritson et al. |
| 5,758,638 A | | 6/1998 | Kreamer |
| 5,794,612 A | | 8/1998 | Wachter et al. |
| 5,809,997 A | * | 9/1998 | Wolf ........................ 128/200.23 |
| 5,842,468 A | | 12/1998 | Denyer et al. |
| 6,039,042 A | * | 3/2000 | Sladek ..................... 128/200.23 |
| 6,192,879 B1 | | 2/2001 | Eskildsen et al. |
| 6,240,917 B1 | | 6/2001 | Andrade |
| 6,571,971 B1 | | 6/2003 | Weiler |
| 6,578,571 B1 | | 6/2003 | Watt |
| 6,830,046 B2 | * | 12/2004 | Blakley et al. ........... 128/200.14 |
| 7,191,777 B2 | * | 3/2007 | Brand et al. .............. 128/200.23 |
| 7,454,267 B2 | * | 11/2008 | Bonney et al. ................ 700/237 |
| 2003/0205229 A1 | | 11/2003 | Crockford et al. |
| 2004/0094151 A1 | * | 5/2004 | Speldrich et al. ........ 128/203.12 |
| 2004/0107961 A1 | * | 6/2004 | Trueba .................... 128/200.16 |
| 2005/0087189 A1 | | 4/2005 | Crockford et al. |
| 2005/0126561 A1 | * | 6/2005 | Grychowski et al. .... 128/200.23 |
| 2006/0130838 A1 | * | 6/2006 | Lee et al. ................. 128/205.23 |
| 2007/0062519 A1 | * | 3/2007 | Wuttke et al. ............ 128/200.14 |
| 2007/0235028 A1 | | 10/2007 | Bruce et al. |
| 2008/0228099 A1 | | 9/2008 | Abrams et al. |
| 2011/0226242 A1 | | 9/2011 | Von Hollen et al. |

FOREIGN PATENT DOCUMENTS

| | | |
|---|---|---|
| WO | 9311817 | 6/1993 |
| WO | 9312823 | 7/1993 |
| WO | 9526212 A1 | 10/1995 |
| WO | 9713553 | 4/1997 |
| WO | 02058771 A1 | 8/2002 |
| WO | 03022332 A2 | 3/2003 |
| WO | 2005123165 A1 | 12/2005 |
| WO | 2008091838 A2 | 7/2008 |
| WO | 2010023591 A2 | 3/2010 |

OTHER PUBLICATIONS

James B. Fink et al; "Problems With Inhaler Use: A Call for Improved Clinician and Patient Education", Respiratory care : the official journal of the American Association for Respiratory Therapy, vol. 50, No. 10, Sep. 2005.

Iles et al, "Crying Significantly Reduces Absorption of Aerosolised Drug in Infants", Arch Dis Child, vol. 18, 1999, pp. 163-165.

O'Callaghan et al, Delivery of Beclomethasone Dipropionate From a Spacer Device: What Dose Is Available for Inhalation?, Thorax, vol. 49, 1994, pp. 961-964.

Pierart et al, "Washing Plastic Spacers in Household Detergent Reduces Electrostatic Charge and Greatly Improves Delivery", Eur Respir J, vol. 13, 1999, p. 673-678.

Hayden et al, "A Randomised Crossover Trial of Facemask Efficacy", Archives of Disease in Childhood, vol. 89, 2004, pp. 72-73.

Usherwood et al, "Questionnaire to Measure Perceived Symptoms and Disability in Asthma", Archives of Disease in Childhood, vol. 65, 1990, pp. 779-781.

Lee-Wong et al, Results of a Programme to Improve House Staff Use of Metered Dose Inhalers and Spacers, Post Graduate Medical Journal, vol. 79, 2003, pp. 221-225.

Byron, "Performance Characteristics of Pressurized Metered Dose Inhalers in Vitro", Journal of Aerosol Medicine, vol. 10, Suppl 1, 1997, pp. S-3-S-6.

Scarpaci et al, "Assessment of Hospice Nurses' Technique in the Use of Inhalers and Nebulizers", Journal of Palliative Medicine, vol. 10. No. 3, 2007, pp. 665-676.

Smith et al, "HFA Fluticasone Propionate: Delivery Via an Antistatic Spacer", American Journal or Respitory Critical Care Medicine, 2002, vol. 165, p. B49.

* cited by examiner

RESPIRATORY DRUG DELIVERY APPARATUS INCLUDING A FEEDBACK AND COMPLIANCE DEVICE

The present invention pertains to an apparatus for delivering a respiratory drug to a patient, and, in particular, to a respiratory drug delivery apparatus that includes a feedback and compliance device which provides feedback to a patient regarding use of the respiratory drug delivery apparatus, particularly in situations where the patient is required to regularly self medicate using the respiratory drug delivery apparatus.

It is well known to deliver a medication to a patient's respiratory system to treat a medical condition using a respiratory drug delivery apparatus. For example, a patient suffering from an acute asthmatic attack may use a respiratory drug delivery apparatus to deliver a bronchodilator, such as albuterol (salbutamol), in the form of a fine mist to the patient's respiratory system.

One known respiratory drug delivery apparatus consists of a metered dose inhaler (MDI) and a spacer or valved holding chamber. The MDI, also known simply as an "inhaler", includes a canister or nebulizer that contains the medication under pressure and a canister holder, commonly called a boot, which is typically "L" shaped. Although it is common for a patient to use the boot as a mouthpiece for receiving the aerosolized medication into their airway directly from the aerosol dispensing leg of the boot, this configuration may not optimize the mixing of the medication with the air because the aerosolized medication is injected directly into the airway. Without adequate mixing of the drug with the air, the medication may not be inhaled into the patient's lungs where it is effective, but may form as droplets that are deposited in the patient's mouth and swallowed without the desired medicinal effect.

To enhance mixing of the medication with air, it is known to provide a spacer, also commonly referred to as a valved holding chamber, that attaches to the aerosol dispending end of the boot. The spacer, which is typically a small hollow cylinder with a one-way valve at the downstream end, receives the aerosol from the canister and allows it to form into a fine mist for inhalation into the airway of the patient. Optionally, a mask may be provided at the end of the spacer opposite the MDI so that the patient can breathe through his or her mouth to receive the medication. Examples of conventional spacers and associated components are shown in U.S. Pat. Nos. 4,470,412; 4,809,692; and 4,832,015 all to Nowacki et al.; U.S. Pat. No. 5,012,803 to Foley et al.; U.S. Pat. No. 5,042,467 to Foley; U.S. Pat. No. 5,385,140 to Smith, U.S. Pat. No. 5,848,599 to Foley et al., and U.S. Pat. No. 6,557,549 to Schmidt et al. Other known respiratory drug delivery apparatuses include dry powder inhalers (DPIs) and nebulizers.

Proper use of a medical device such as a respiratory drug delivery apparatus is essential, particularly in situations where a patient is required to regularly self-medicate to manage their disease condition. This is often the case in respiratory disease situations where the patient is typically provided with a respiratory drug delivery apparatus and is expected to self-manage their respiratory disease condition using the respiratory drug delivery apparatus. Normally, a medical professional will provide the initial education to the patient as to how to use the respiratory drug delivery apparatus in order to self-administer the respiratory medication properly. As will be appreciated, the effectiveness of this method of training is largely based on the knowledge and skill level of the medical professional as well as the amount of time that this professional can spend with the patient, which is often limited.

In the area of respiratory drug delivery, a number of assessments have been conducted to quantify the knowledge level of medical professionals on the proper administration of medication using a respiratory drug delivery apparatus such as an MDI or an MDI with a valved holding chamber. Unfortunately, such assessments have not been encouraging. One particular study involving medical professionals indicated that the percentage of participants that correctly completed the proper steps for use of an MDI alone was 67.6%, the percentage of participants that correctly completed the proper steps for use of an MDI with a spacer was 49.9%, and the percentage of participants that correctly completed the proper steps for use of a nebulizer was 38%. This study was reported in Laura T. Scarpati, Pharm.D., "*Assessment of Hospice Nurses' Technique in the Use of Inhalers and Nebulizers,*" Palliative Medicine Vol. 10, No. 2, 2007. Another study directed to medical professionals in a hospital setting relating to MDI and spacer use showed that only 5% used an MDI perfectly. This improved to 13% after a lecture and demonstration and 73% after intensive one-on-one sessions. This study was reported in M Lee-Wong, "*Results of a Programe to Improve House Staff Use of Metered Dose Inhalers and Spacers,*" Post Graduate Medical Journal, Vol. 79, pages 221-225, 2003.

Another study was conducted in order to quantify the knowledge level of patients on the administration of medication using an MDI alone. The results indicated that 28%-68% of patients do not effectively use their MDI. In addition, a patient's reading level has been correlated to improper techniques in using an MDI. Specifically, poor technique, identified as less than or equal to three correct steps being performed, was found on 89% of patients who read at the third grade level and 48% of patients who read at the high school level. This study was reported in James B. Fink, "*Problem with Inhaler Use: A Call for Improved Clinician and Patient Education,*" Respiratory Care, Vol. 50, No. 10, September 2005.

Moreover, medical devices such as respiratory drug delivery apparatuses are typically provided with a set of written instructions. However, such instructions are in many cases never read by the patient and/or not consulted and/or used during use of the device (patients may dispose of the instructions or store the instructions separately from the device itself).

Thus, it is evident that there is a long felt but unresolved need for a respiratory drug delivery apparatus which enhances treatment by encouraging proper use of the apparatus by the patient. This is particularly true in situations which require patients to self-medicate separate from the oversight of a health professional, as is often the case with respiratory disease management.

In one embodiment, a respiratory drug delivery apparatus is provided that includes a medication storage and delivery device, such as a metered dose inhaler, a dry powder inhaler or an aqueous liquid dispensing system, having an outlet and a feedback and compliance device coupled to the medication storage and delivery device. The feedback and compliance device has an opening, and the outlet of the medication storage and delivery device is received through the opening. The feedback and compliance device includes: (i) one or more sensors, each of the one or more sensors being structured to sense a parameter relating to use of the respiratory drug delivery apparatus without modifying or interfering with a flow of medication introduced by actuation of the medication storage and delivery device, (ii) one or more feedback devices, and (iii) a processing unit programmed to cause the one or more feedback devices to provide feedback information to a patient regarding use of the respiratory drug delivery apparatus based on an output of at least one of the one or more sensors. The feedback information may be audible, visual, or tactile, or any combination thereof.

In another embodiment, a method of encouraging proper use of a respiratory drug delivery apparatus including a medication storage and delivery device is provided. The method includes providing a feedback and compliance device, wherein the feedback and compliance device includes one or more sensors, each of the one or more sensors being structured to sense a parameter relating to use of the respiratory drug delivery apparatus without modifying or interfering with a flow of medication introduced by actuation of the medication storage and delivery device, coupling the medication storage and delivery device to the feedback and compliance device by inserting an outlet of the medication storage and delivery device through an opening provided in the feedback and compliance device, and providing feedback information to a patient regarding use of the respiratory drug delivery apparatus based on an output of at least one of the one or more sensors.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

Figure 1:
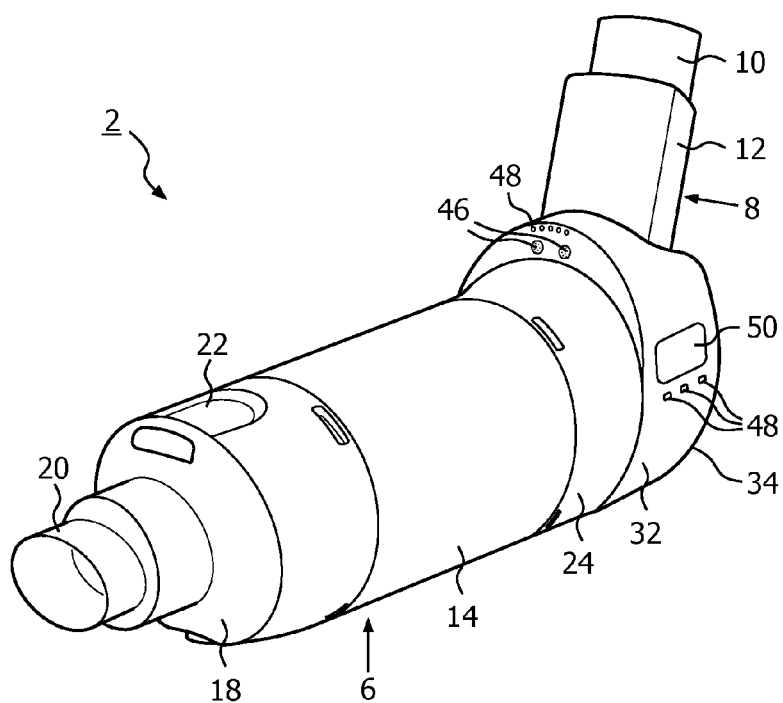
FIGS. 1 and 2 are front and rear isometric views, respectively, of a respiratory drug delivery apparatus according to one particular embodiment of the invention.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed, herein, the statement that two or more parts or components are "coupled" together shall mean that the parts are joined or operate together either directly or through one or more intermediate parts or components.

As employed herein, the statement that two or more parts or components "engage" one another shall mean that the parts exert a force against one another either directly or through one or more intermediate parts or components.

As employed herein, the term "number" shall mean one or an integer greater than one (i.e., a plurality).

Figure 2:
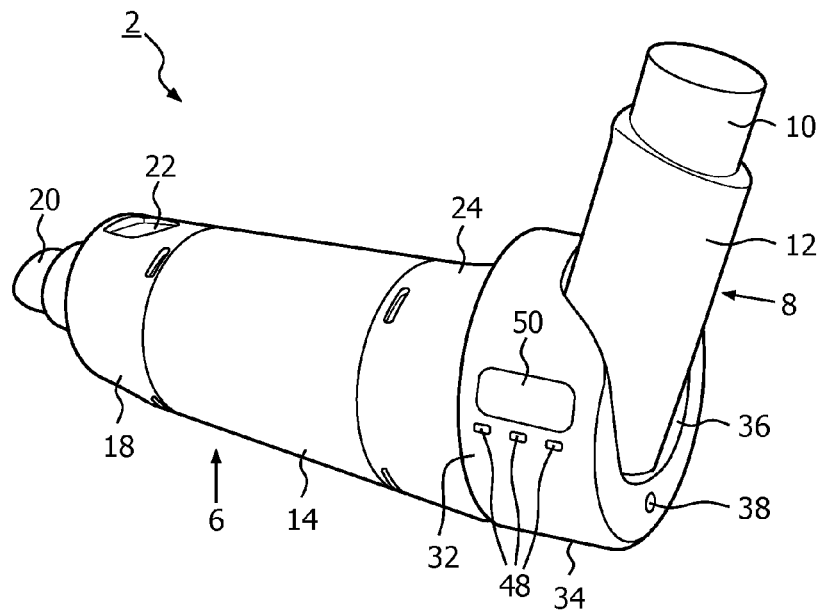
Figure 3:
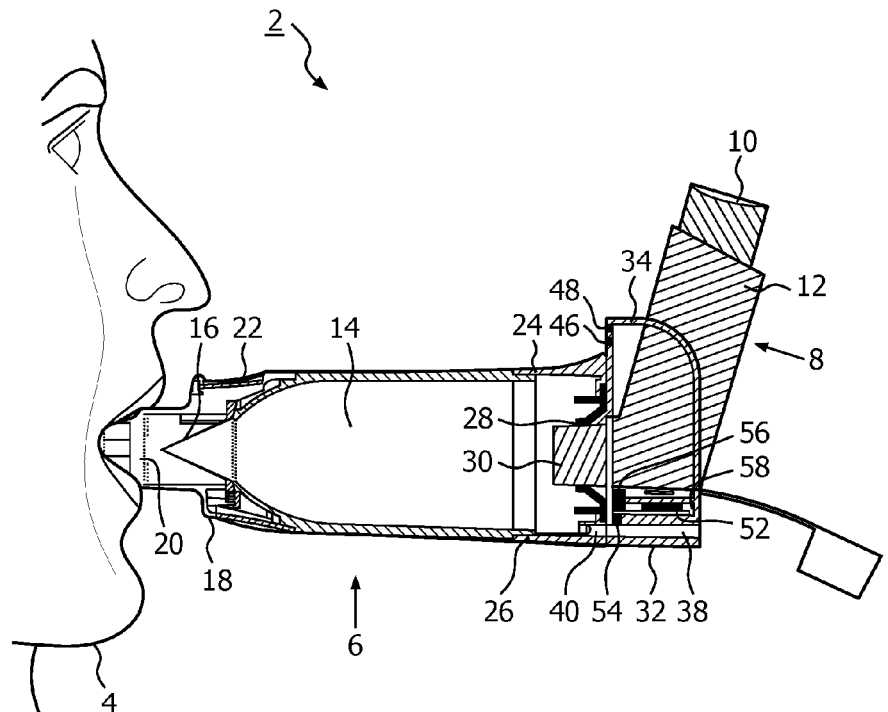
FIG. 3 is a side cross-sectional view of the respiratory drug delivery apparatus of FIGS. 1 and 2 inserted into the mouth of a patient.

FIGS. 1 and 2 are front and rear isometric views, respectively, of respiratory drug delivery apparatus 2 according to one particular embodiment of the invention. FIG. 3 is a side cross-sectional view of respiratory drug delivery apparatus 2 inserted into the mouth of patient 4. Respiratory drug delivery apparatus 2 includes valved holding chamber 6 that is structured to be used in connection with metered dose inhaler (MDI) 8 having canister 10 received within boot 12 as described elsewhere herein. Valved holding chamber 6 includes generally cylindrical main chamber 14 having one-way inhalation valve 16 (FIG. 3), such as an elastomeric duck-bill valve, coupled to the front end thereof. In one exemplary embodiment, main chamber 14 is made of a clear, antistatic material. In addition, mouthpiece assembly 18 is coupled to the front end of main chamber 14 and includes mouthpiece 20 structured to be received within the lips of patient 4 during use of respiratory drug delivery apparatus 2 and exhalation valve element 22 operatively coupled thereto, which in the illustrated embodiment is in the form of a flap exhalation valve.

Respiratory drug delivery apparatus 2 further includes two-part MDI adapter 24 which is structured to be removeably attached to the end of main chamber 14 that is opposite mouthpiece assembly 18 (i.e., the rear end). MDI adapter 24 is structured to receive and hold MDI 8. The two-part MDI adapter 24 includes rigid end cap 26 made of, for example, a hard plastic or some other suitable rigid material that is structured to be selectively attachable to the rear end of main chamber 14. Two-part MDI adapter 24 further includes flexible inner portion 28 made of a flexible material, such as, without limitation, silicone, rubber, TPE, or foam, among other suitable materials. Inner portion 28 is structured to be received in and held by end cap 26 and may be made to be removable so that it can be cleaned and/or replaced if damaged, or, alternatively, may be permanently affixed to the end cap 26 by a process such as an over-molding process. Flexible inner portion 28 includes walls which define an aperture structured to receive outlet 30 of boot 12 of MDI 8. The flexible nature of inner portion 28 enables it to hold MDIs of different shapes and sizes.

As is known in the art, and as described in more detail herein in connection with one particular embodiment of the invention, when valved holding chamber 6 is used by patient 4, patient 4 shakes MDI 8 and valved holding chamber 6, inserts mouthpiece 20 into his or her mouth and exhales in order to at least partially empty gas from the lungs. The exhaled gasses are, through operation of the exhalation valve element 22, allowed to flow from within mouthpiece assembly 18 to the ambient atmosphere through one or more exhalation ports that are covered by the exhalation valve element 22. Such gasses are not, as a result of the operation of one-way inhalation valve 16 provided within main chamber 14, permitted to flow into the interior of main chamber 14. Following exhalation, patient 4 actuates MDI 8 in order to cause a dose of medication (in the form of an aerosol plume) to be sprayed within main chamber 14, and thereafter begins inhaling. During inhalation, one-way inhalation valve 16 permits fluid flow from within main chamber 14 into mouthpiece assembly 18 and out through mouthpiece 20 so that the medication (mixed with air in main chamber 14) may be deposited within the lungs of patient 4. This process may be repeated one or more times depending on the needs of the particular patient.

Figure 9:
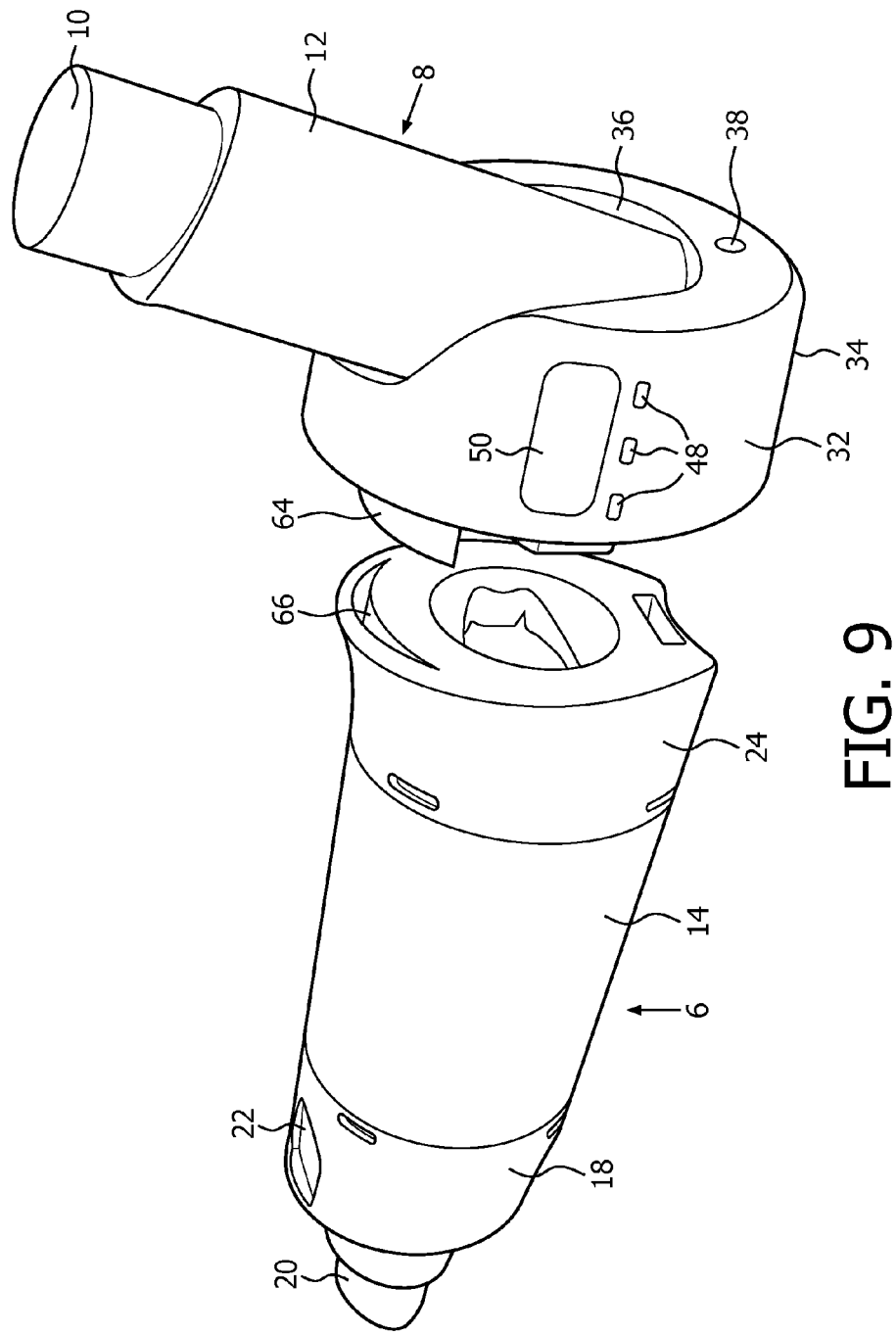
FIG. 9 is a front isometric view of a respiratory drug delivery apparatus according to another particular embodiment of the invention.

Respiratory drug delivery apparatus 2 further includes feedback and compliance device 32 that is removeably coupled to the rear end of MDI adapter 24. The feedback and compliance device 32 may be coupled to the rear end of MDI adapter 24 by a mechanical connecting mechanism or an adhesive. For example, FIG. 9 shows one particular embodiment wherein feedback and compliance device 32 is able to be selectively coupled to the rear end of MDI adapter 24 using a mechanical connecting mechanism that includes connector 64 extending from feedback and compliance device 32 that is structured to be received and held within slot 66 provided in MDI adapter 24. Alternatively, feedback and compliance device 32 may be coupled to the rear end of MDI adapter 24 and held in place as a result of outlet 30 of boot 12 being held by inner portion 28 of MDI adapter 24, in which case feedback and compliance device 32 will be held and sandwiched between MDI adapter 24 and MDI 8. In an alternative embodiment, feedback and compliance device 32 may be incorporated as part of MDI adapter 24 in a one piece assembly. This would allow the patient or caregiver to readily exchange such a one piece assembly with an existing chamber adapter.

Feedback and compliance device 32 includes outer housing 34, which in the exemplary embodiment is made of a rigid material such as a hard plastic or some other suitable rigid material. Outer housing 34 includes central recess 36 that is structured to receive the bottom of boot 12 of MDI 8, and includes an opening so that the bottom of boot 12, and specifically outlet 30 of boot 12 of MDI 8, can be inserted through outer housing 34 and received and held by flexible inner portion 28 (FIG. 3). As described in greater detail herein, feedback and compliance device 32 is structured to automatically monitor the use of respiratory drug delivery apparatus 2 by patient 4 and provide feedback in the form of instructions and compliance information regarding the proper use of respiratory drug delivery apparatus 2 to patient 4 without interfering with the dispensing of medication from canister 10 of MDI 8 (e.g., the amount of dose delivered will not be effected). Outer housing 34 also includes channel 38 that is in fluid communication with channel 40 provided in end cap 26 of MDI adapter 24 when feedback and compliance device 32 coupled to the rear end of MDI adapter 24. The purpose of channels 38 and 40 is described elsewhere herein.

Figure 4:
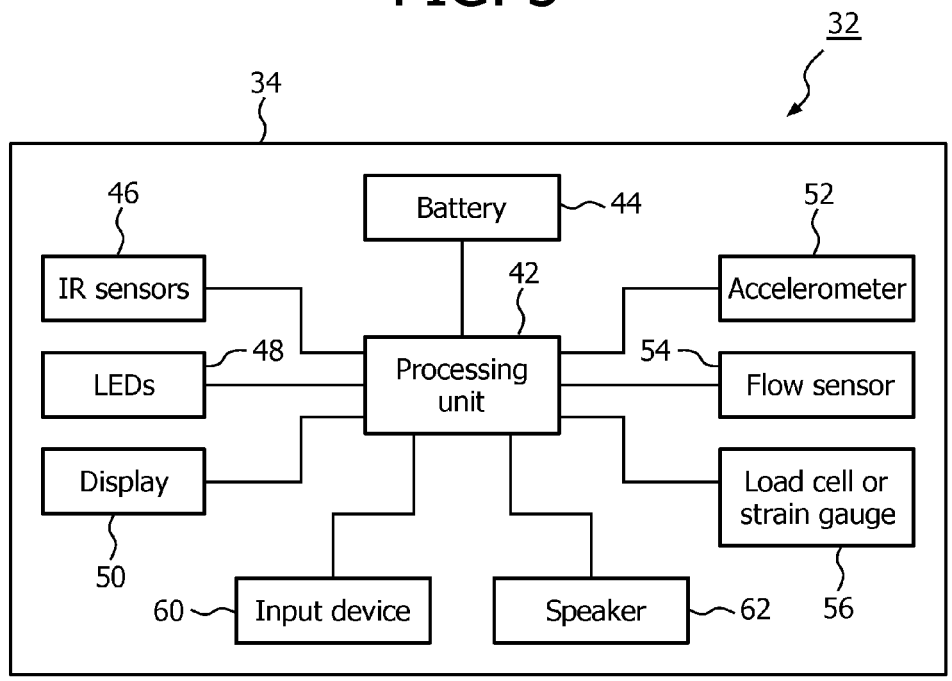
FIG. 4 is a block diagram of the feedback and compliance device of the respiratory drug delivery apparatus of FIGS. 1 and 2 according to one particular embodiment.

FIG. 4 is a block diagram of feedback and compliance device 32 showing selected components thereof according to one particular embodiment. The positioning of certain of those components so as not to interfere with the dispensing of medication from canister 10 of MDI 8 in this particular embodiment is shown in FIG. 3. Feedback and compliance device 32 includes processing unit 42, which may include a microprocessor, a microcontroller, or any other suitable processor, which is operatively coupled to a suitable memory for storing programs/routines to be executed by processing unit 42. Specifically, the memory, which may be separate from and/or internal to the microprocessor, microcontroller or other suitable processor, stores one or more routines for controlling the operation of feedback and compliance device 32 as described in greater detail elsewhere herein. Feedback and compliance device 32 also includes battery 44 or a similar power supply for providing power to the components of feedback and compliance device 32.

Figure 5:
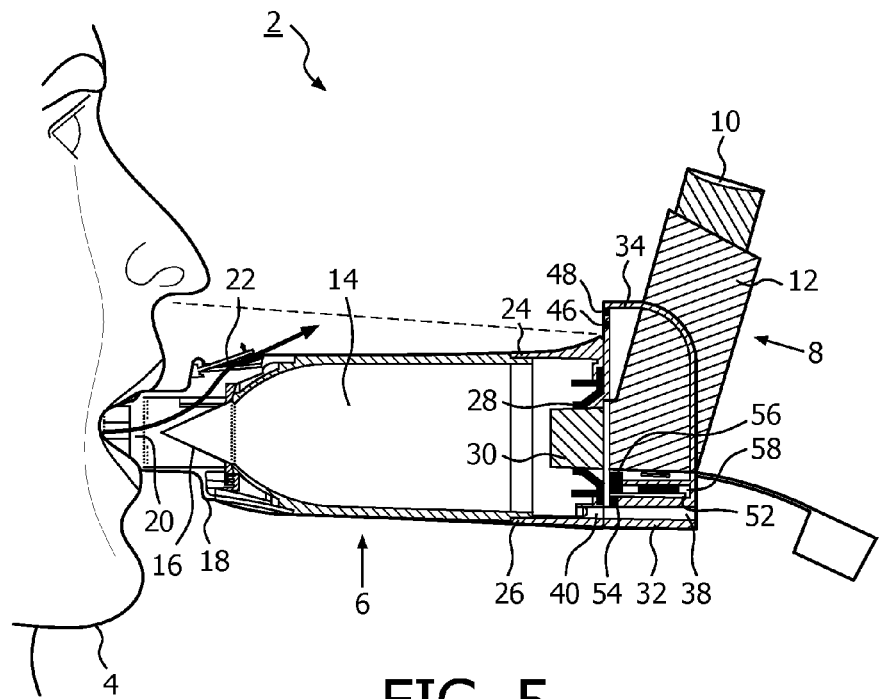
FIGS. 5-7 are side cross-sectional views of the respiratory drug delivery apparatus of FIGS. 1 and 2 inserted into the mouth of a patient which illustrate various aspect of the operation of the respiratory drug delivery apparatus.

One or more IR sensors 46 are operatively coupled to processing unit 42. In the exemplary embodiment, as seen in FIGS. 1 and 3, two IR sensors 46 are provided on a top portion of the front end of outer housing 34. Referring to FIG. 5, the first one of the IR sensors 46 is structured to sense the distance between the front end of outer housing 34 and the face of patient 4, as indicated by the dotted line in FIG. 5, to determine whether respiratory drug delivery apparatus 2 is being held in position in front of the face of patient 4. As described in greater detail below, this information may be used in connection with fluid flow information to determine whether patient 4 is holding his or her breath as instructed. Also referring to FIG. 5, the second one of the IR sensors 46 is structured to sense operation of exhalation valve element 22 and thus exhalation by patient 4 as indicated by the arrow in FIG. 5 by sensing movement of exhalation valve element 22 or sound or air temperature moving through exhalation valve element 22.

In addition, one or more LEDs 48 and display 50, such as an LCD, are operatively coupled to processing unit 42. In the exemplary embodiment, as seen in FIGS. 1 and 3, a first plurality of LEDs 48 are provided on the top portion of the front end of outer housing 34, and a second plurality of LEDs 48 and display 50 in the form of an LCD are provided on the side of outer housing 34. LEDs 48 and display 50 are structured to provide visual information such as feedback and instructions to patient 4 as described in greater detail herein. Optionally, a tactile feedback device, such as a vibrator, may be coupled to processing unit 42 to provide feedback and instructions to patient 4 that are tactile in nature.

Feedback and compliance device 32 also includes a number of additional sensors that are operatively coupled to processing unit 42. In particular, an accelerometer 52 or another suitable motion sensing device is provided as part of feedback and compliance device 32 for sensing when respiratory drug delivery apparatus 2 is being shaken or otherwise moved by patient 4. In the exemplary embodiment shown in FIG. 3, accelerometer 52 is provided in channel 58 provided in outer housing 34 above channel 38.

Figure 6:
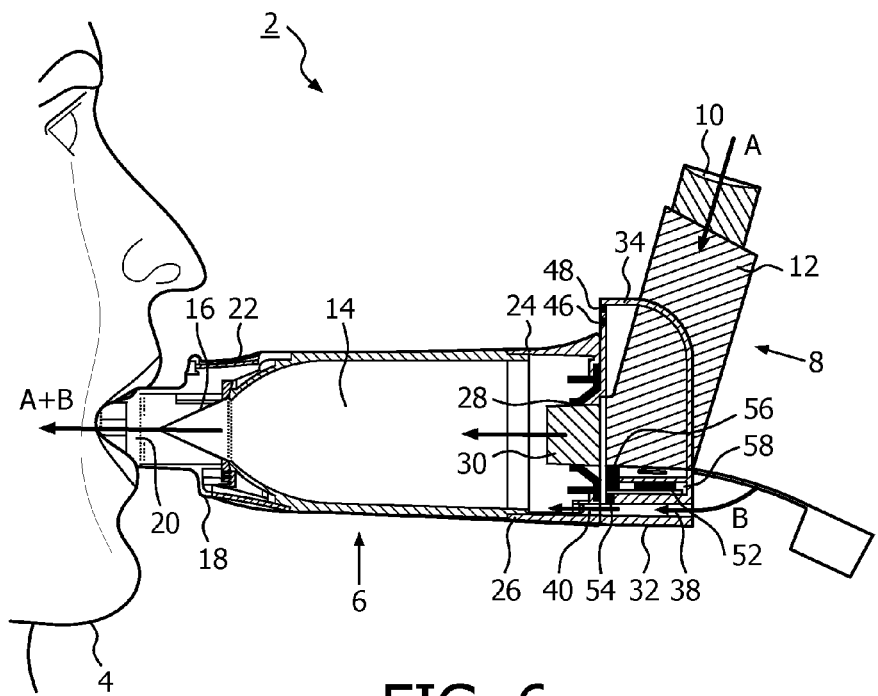

In addition, flow sensor 54 is provided as part of feedback and compliance device 32 for sensing fluid flow through channels 38 and 40 and main chamber 14, and thus inhalation by patient 4. In the exemplary embodiment shown in FIG. 3, flow sensor 54 is provided adjacent to channel 38 in outer housing 34. Flow sensor 54 may be, without limitation, a micro-electro-mechanical system (MEMS) type flow sensor. Referring to FIG. 6, the fluid flow resulting from actuation of MDI 8 is shown by the arrow A and air flow through channels 38 and 40 due to inhalation is shown by the arrow B. Alternative methods and mechanisms for sensing inhalation by patient 4 may also be employed. For example, a pressure differential between outlet 30 and channel 40 may be monitored, which differential will change when patient 4 is inhaling. Also, an acoustic microphone may be provided in housing 34 to listen for and detect sounds indicative of inhalation by patient 4. As another alternative, a temperature sensor may be provided in housing 34 to monitor the temperature within main housing 14 and detect a temperature change resulting from removal of the aerosol plume introduced by actuation of MDI 8 due to inhalation by patient 4. As another alternative, an infrared (IR) sensor or acoustic motion sensor may be provided in housing 34 to detect movement of one-way inhalation valve 16 due to inhalation by patient 4.

Figure 7:
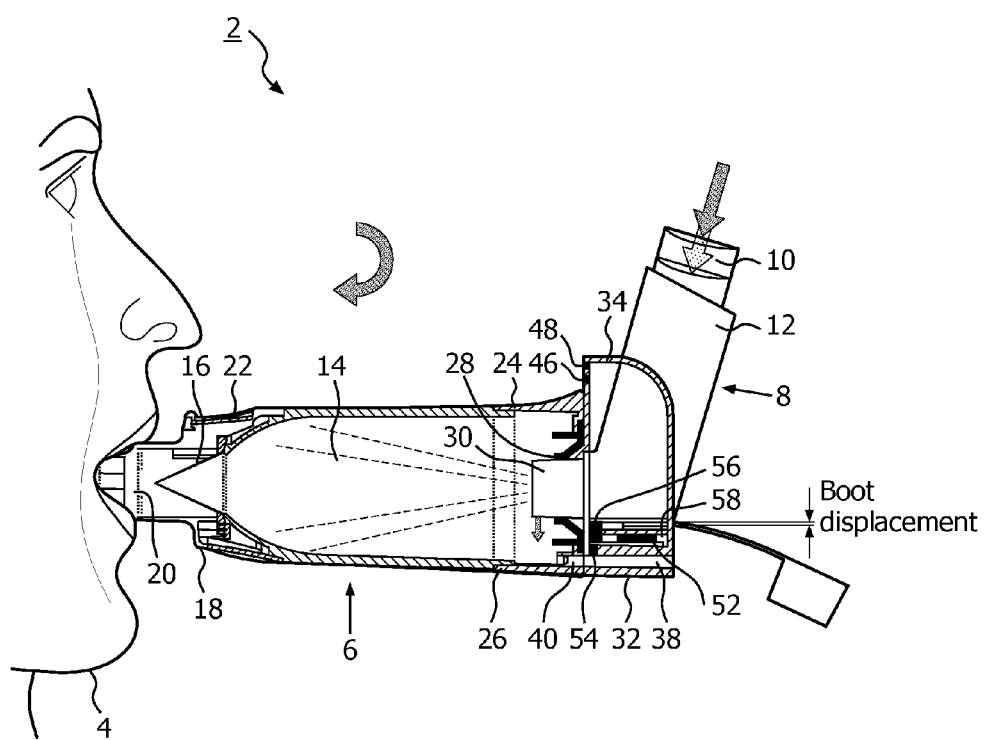

Finally, load cell or strain gauge 56 is provided as part of feedback and compliance device 32 for sensing generally downward forces applied thereto by boot 12 of MDI 8. Such downward forces may result from insertion of MDI 8 into feedback and compliance device 32 and actuation or firing of MDI 8 by patient 4 (wherein detection of associated forces may be used to detect such actions). In the exemplary embodiment shown in FIG. 3, load cell or strain gauge 56 is provided adjacent to channel 58 in outer housing 34. Referring to FIG. 7, the displacement of boot 12 due to the force that is applied to canister 10 to actuate or fire MDI 8 is shown by the arrows located adjacent boot 12 (boot 12 is able to pivot with respect to outer housing 34 due to the flexible nature of inner portion 28). The force resulting from that displacement is able to be detected by load cell or strain gauge 56, or another type of suitable force detecting device.

Alternative methods and mechanisms for sensing actuation or firing of MDI 8 by patient 4 may also be employed. For example, an acoustic microphone may be provided in housing 34 to listen for and detect sounds indicative of actuation or firing of MDI 8. As another alternative, a temperature sensor may be provided in housing 34 to monitor the temperature within main housing 14 and detect a temperature change (reduction) resulting from introduction of the aerosol plume by actuation of MDI 8. As another alternative, accelerometer 52 may be used to detect movement of MDI 8 and therefore respiratory drug delivery apparatus 2 resulting from the downward force applied to canister 10 to actuate MDI 8. As still another alternative, an IR emitter and detector may be used to detect the presence of the aerosol being ejected from MDI 8 (the aerosol would disrupt the light beam). In particular, the emitter/detector pair would be positioned inside of or on the outside of main chamber 14 with an orientation that is perpendicular to the aerosol plume, and, in one exemplary embodiment where feedback and compliance device 32 is combined with MDI adapter 24 as a one piece assembly (described above), they would be part of feedback and compliance device 32.

In addition, alternative methods and mechanisms for sensing insertion of MDI 8 into feedback and compliance device 32 may also be employed. For example, and as described in U.S. Provisional Application No. 61/091,546, owned by the assignee hereof, a flexible, resilient tab actuating member may be provided which extends from outer housing 34 and which is structured to extend partially over central recess 36. When MDI 8 is inserted into feedback and compliance device 32, the tip of the tab actuating member is pushed downwardly and against a switch that is coupled to processing unit 42. Actuation of the switch in this embodiment indicates insertion of the MDI 8.

Breath hold by patient 4 may, in one particular embodiment, be detected and verified using flow sensor 54 and IR sensors 46 and/or accelerometer 52. In one embodiment, processing unit 42 may detect and verify (and time) that patient 4 is holding his or her breath by sensing the end of an inhalation action using flow sensor 54, and determining that each of the following is true: (i) patient 4 has not exhaled through exhalation valve element 22 as determined by one of the IR sensors 46 (described elsewhere herein), (ii) patient 4 has not moved respiratory drug delivery apparatus 2 and is holding respiratory drug delivery apparatus 2 in place as shown in FIG. 5 as determined by accelerometer 52, and (iii) patient has not started another inhalation action as determined flow sensor 54. In another embodiment, processing unit 42 may detect and verify (and time) that patient 4 is holding his or her breath by sensing the end of an inhalation action using flow sensor 54, and determining that each of the following is true: (i) patient 4 has not exhaled through exhalation valve element 22 as determined by one of the IR sensors 46 (described elsewhere herein), (ii) patient 4 is holding respiratory drug delivery apparatus 2 in place as shown in FIG. 5 as determined by another one of the IR sensors 46 (described elsewhere herein), and (iii) patient has not started another inhalation action as determined flow sensor 54. The purpose of the breath hold determination is described elsewhere herein in connection with FIGS. 8A and 8B.

Furthermore, in the exemplary embodiment, feedback and compliance device 32 includes input device 60, such as a button or buttons or a touch screen, for enabling patient 4 to input information into processing unit 42. Feedback and compliance device 32 also includes speaker 62 operatively coupled to processing unit 42 for providing audible outputs, such as instructions or other feedback as described elsewhere herein, to patient 4.

Figure 8A:
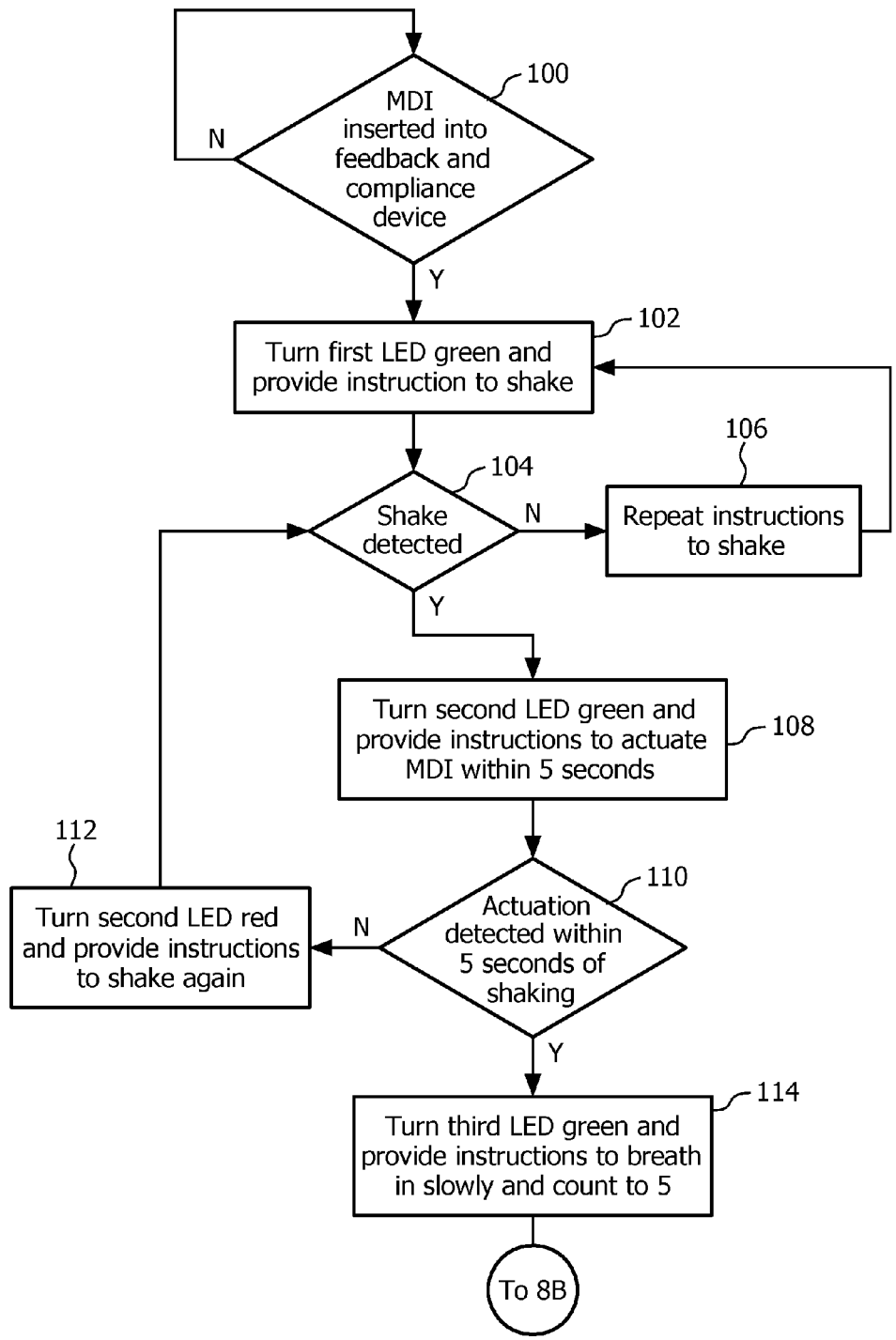
FIGS. 8A and 8B are a flowchart illustrating operation of the respiratory drug delivery apparatus of FIGS. 1-7 according to one particular, non-limiting embodiment of the invention.
Figure 8B:
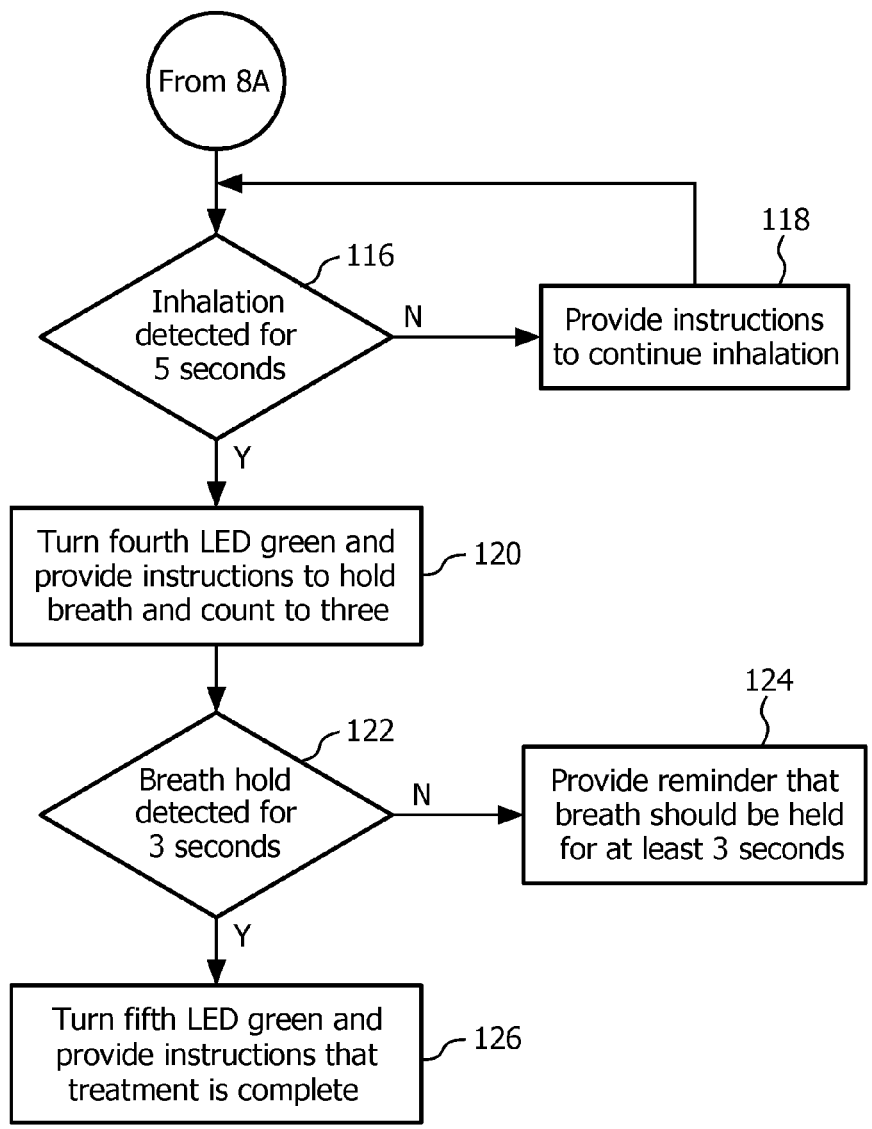

FIGS. 8A and 8B are a flowchart illustrating operation of respiratory drug delivery apparatus 2 according to one particular, non-limiting embodiment of the invention. The method illustrated in FIGS. 8A and 8B is, in the exemplary embodiment, implemented in one or more programs/routines that are stored in and executable by processing unit 42 of feedback and compliance device 32. The method begins at step 100, wherein a determination is made as to whether MDI 8 has been inserted into the feedback and compliance device 32. As described elsewhere herein, that determination may be made based upon a detection of a force associated with such insertion by load cell or strain gauge 56 or by another automatic detecting mechanism such as a tab actuating member and associated switch provided as part of feedback and compliance device 32. Alternatively, that determination may be made in response to patient 4 actuating a part of input device 60 (e.g., pressing a button forming part of input device 60) to indicate that MDI 8 has been inserted and that treatment may begin. If the answer at step 100 is yes, then, at step 102, processing unit 42 causes a first LED to be turned green (for example from an initial red state) and causes an audio instruction instructing patient 4 to shake respiratory drug delivery apparatus 2 to be provided through speaker 62. Next, at step 104, processing unit 42 makes a determination as to whether shaking of respiratory drug delivery apparatus 2 has been detected. As described elsewhere herein, shaking may be detected using a accelerometer 52. If the answer at step 104 is no, then, at step 106, the instructions to shake are repeated and the method returns to step 102. If, however, the answer at step 104 is yes, then, at step 108, processing unit 42 causes a second LED 48 to be turned green (for example from an initial red state) and causes audible instructions instructing patient 4 to actuate MDI 8 within a predetermined time, such as five seconds, to be provided through speaker 62. At step 110, processing unit 42 determines whether MDI 8 has actually been actuated within the predetermined time (e.g., within five seconds of being shaken). As described elsewhere herein, this may be done by sensing the forces caused by such actuation using load cell or strain gauge 56.

If the answer at step 110 is no, then, at step 112, the second LED 48 is turned red by processing unit 42 and processing unit 42 causes audible instructions to shake respiratory drug delivery apparatus 2 to again be provided through speaker 62. The method then returns to step 104. If, however, the answer at step 110 is yes, then, at step 114, processing unit 42 causes a third LED 48 to be turned green (for example from an initial red state) and causes audible instructions instructing patient 4 to breath in slowly and count to a predetermined number, such as five, to be provided through speaker 62. The method then proceeds to step 116 of FIG. 8B. At step 116, processing unit 42 makes a determination as to whether inhalation by patient 4 has been detected for at least a predetermined period such as five seconds. As described elsewhere herein, inhalation may be detected using flow sensor 54. If the answer at step 116 is no, then, at step 118, processing unit 42 causes instructions instructing patient 4 to continue inhalation to be provided through speaker 62. The method then returns to step 116.

If the answer at step 116 is yes, meaning that inhalation for at least the predetermined period (e.g., five seconds) has been detected, then, at step 120, processing unit 42 causes a fourth LED 48 to be turned green (for example from an initial red state) and causes audible instructions instructing patient 4 to hold his or her breath and count to a predetermined number, such as three, to be provided through speaker 62. Next, at step 140, processing unit 42 makes a determination as to whether a breath hold of at least a predetermined time period, such as three seconds, has been detected. In the exemplary embodiment, breath hold is detected as described elsewhere herein using IR sensors 46 and flow sensor 54 and/or accelerometer 52 (FIG. 5). If the answer at step 140 is no, then, at step 145, processing unit 42 causes an audible reminder to be provided through speaker 62 that indicates that the patient 4 should hold his or her breath for at least a predetermined period of time, such as three seconds, when using respiratory drug delivery apparatus 2. If the answer at step 140 is yes, then, at step 150, processing unit 42 causes a fifth LED 48 to be turned green (for example from an initial red state) and causes audible instructions indicating that treatment is complete to be provided through speaker 62.

Optionally, processing unit 42 may be programmed to store information relating to use of respiratory drug delivery apparatus 2 during one or more treatment sessions. Such stored information may include for one or more treatment sessions information relating to whether each step of operating respiratory drug delivery apparatus 2 was properly performed (e.g., whether the LEDs were turned green), and the timing and length of such steps (e.g., how long MDI 8 was shaken, how long after MDI 8 was shaken MDI 8 was then actuated, the length of detected inhalation, and the length of detected breath hold). That information may then be downloaded and reviewed and/or analyzed by patient 4 and/or a caregiver of patient 4.

Figure 10:
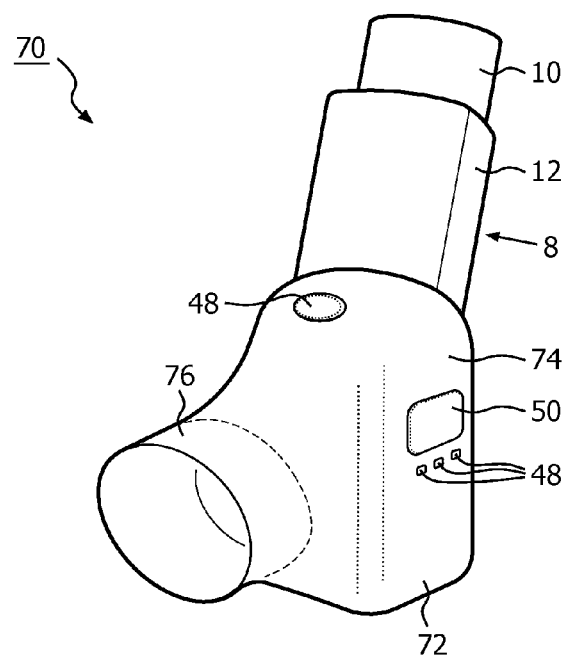
FIGS. 10 and 11 are front and rear isometric views, respectively, of a respiratory drug delivery apparatus according to an alternative exemplary embodiment of the invention.
Figure 11:
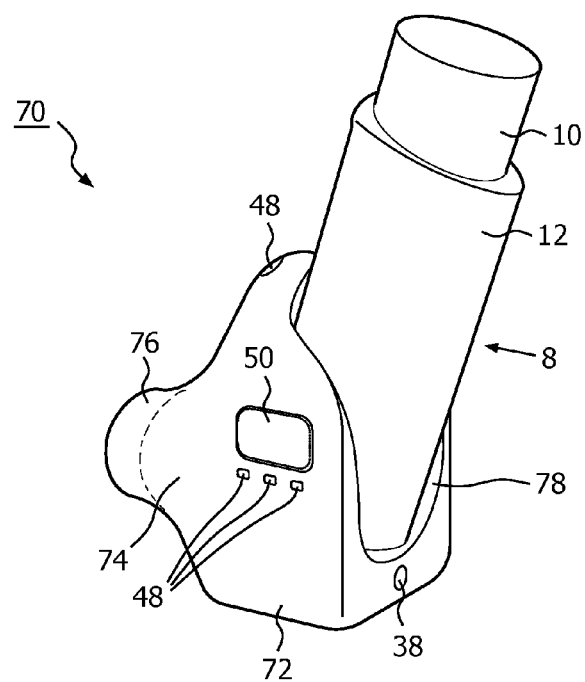
Figure 12:
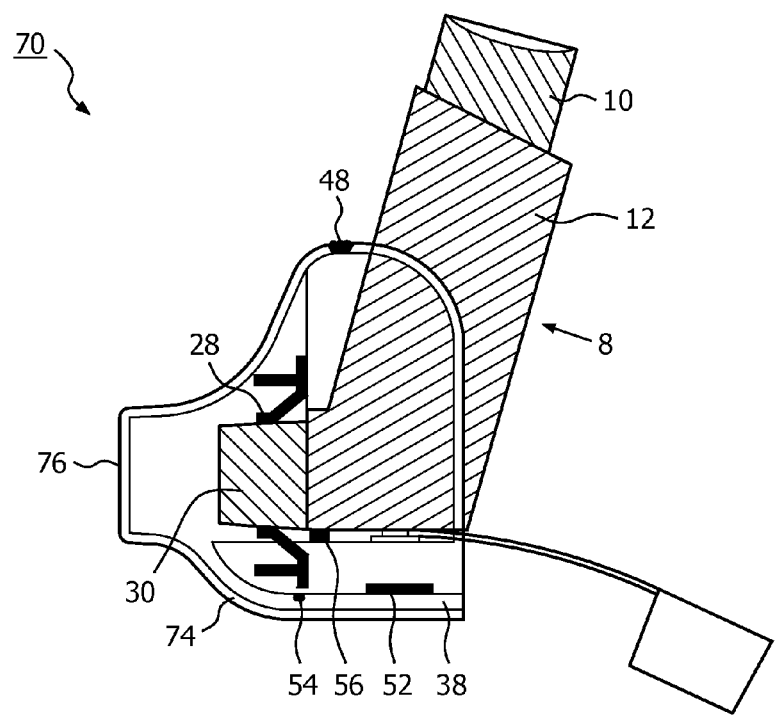
FIG. 12 is a side cross-sectional view of the respiratory drug delivery apparatus of FIGS. 10 and 11.

FIGS. 10 and 11 are front and rear isometric views, respectively, of respiratory drug delivery apparatus 70 according to an alternative exemplary embodiment of the invention. FIG. 12 is a side cross-sectional view of respiratory drug delivery apparatus 70. In the embodiment of FIGS. 10-12, respiratory drug delivery apparatus 70 includes only MDI 8 that is coupled to feedback and compliance device 72. In other words, the embodiment of FIGS. 10-12 does not require a spacer or valved holding chamber to be used with MDI 8. Feedback and compliance device 72 of respiratory drug delivery apparatus 70 is similar in functionality to feedback and compliance device 32, and in the exemplary embodiment includes within housing 74 thereof all of the components of feedback and compliance device 32 shown in FIG. 4 and described elsewhere herein (like components are labeled with like reference numbers). Referring to FIG. 12, feedback and compliance device 72 includes flexible inner portion 28 mounted and supported within rigid housing 74. Flexible inner portion 28 includes walls which define an aperture structured to receive outlet 30 of boot 12 of MDI 8 as described elsewhere herein when boot 12 is received through central recess 78 of housing 74. Feedback and compliance device 72 also includes a mouthpiece 76 on a front end of housing 74 such that a central channel for medication flow exists through housing 74. As noted above, feedback and compliance device 72 is structured to provide all of the feedback and compliance functionality of feedback and compliance device 32 described elsewhere herein. Feedback and compliance device 72 thus provides a device for providing that functionality that can be directly coupled to MDI 8 and used without a valved holding chamber or spacer, as a patient can receive the medication directly through mouthpiece 76.

While the exemplary embodiments of the present invention described elsewhere herein each employ a medication storage and delivery device in the form of a metered dose inhaler (MDI), it is to be understood that that is meant to be exemplary only and is not meant to be limiting. Other types of known or hereafter developed medication storage and delivery devices may be also employed with feedback and compliance device 32 or feedback and compliance device 72. For example, and without limitation, feedback and compliance device 32 or feedback and compliance device 72 may be coupled to and used with a dry powder inhaler (DPI) or an aqueous liquid dispensing system.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A respiratory drug delivery apparatus, comprising:
 a medication storage and delivery device having an outlet, the medication storage and delivery device being a metered dose inhaler having a canister received in a boot, the outlet being part of the boot; and
 a feedback and compliance device coupled to the medication storage and delivery device, and coupled to a valved holding chamber, wherein the valved holding chamber includes a main chamber, an adapter coupled to the main chamber, and an exhalation valve, and wherein:
 the feedback and compliance device is structured to be removable attached to the adapter via a connector extending from the feedback and compliance device, the connector being structured to be received and held within a slot provided in the adapter;
 the adapter receives and holds the outlet of the boot of the metered dose inhaler, wherein the feedback and compliance device is held and positioned between a portion of the metered dose inhaler and the adapter; and
 the feedback and compliance device has an opening, the outlet of the medication storage and delivery device being received through the opening, the feedback and compliance device including:
  (i) one or more sensors, individual ones of the one or more sensors being structured to sense a parameter relating to use of the respiratory drug delivery apparatus without modifying or interfering with a flow of medication introduced by actuation of the medication storage and delivery device, wherein the one or more sensors include an infra-red sensor for sensing air temperature moving through the exhalation valve, and an infra-red sensor for sensing a position of the respiratory drug delivery apparatus relative to a face of a patient;
  (ii) one or more feedback devices, and
  (iii) a processing unit programmed to cause the one or more feedback devices to provide feedback information to a patient regarding use of the respiratory drug delivery apparatus based on an output of at least one of the one or more sensors, wherein the processing unit is programmed to cause the one or more feedback devices to provide feedback information in the form of audible instructions.

2. The respiratory drug delivery apparatus according to claim 1, wherein the feedback information is, visual, or tactile, or a combination thereof.

3. The respiratory drug delivery apparatus according to claim 1, wherein the one or more sensors include one or more of (i) a motion sensing device for sensing shaking of the medication storage and delivery device, (ii) a flow sensor for sensing inhalation by the patient, or (iii) a force sensing device for sensing actuation of the medication storage and delivery device.

4. The respiratory drug delivery apparatus according to claim 3, wherein the motion sensing device is an accelerometer, wherein the flow sensor is a micro-electro-mechanical system flow sensor, and wherein the force sensing device is a load cell or a strain gauge.

5. The respiratory drug delivery apparatus according to claim 3, wherein the processing unit is programmed to cause the one or more feedback devices to provide feedback information in the form of: (i) an instruction to shake the medication storage and delivery device in response to determining that the medication storage and delivery device has been inserted into the feedback and compliance device, (ii) an instruction to actuate the medication storage and delivery device in response to determining that the medication storage and delivery device has been shaken, (iii) an instruction to inhale in a first particular manner in response to determining that the medication storage and delivery device has been actuated, and (iv) an instruction whereby the patient is instructed to hold his or her breath in a second particular manner in response to determining that inhalation in the first particular manner has been completed.

6. The respiratory drug delivery apparatus according to claim 3, wherein the processing unit is programmed to cause the one or more feedback devices to provide feedback information in the form of: (i) a first indication indicating that the medication storage and delivery device has been properly inserted into the feedback and compliance device in response to determining that the medication storage and delivery device has been inserted into the feedback and compliance device, (ii) a second indication indicating that the medication storage and delivery device has been properly shaken in response to determining that the medication storage and delivery device has been shaken, (iii) a third indication indicating that the medication storage and delivery device has been properly actuated in response to determining that the medication storage and delivery device has been actuated, (iv) a fourth indication indicating that inhalation has been properly performed in response to determining that inhalation in a first particular manner has been completed, and (v) a fifth indication indicating that breath hold has been properly performed in response to determining that the patient has held his or her breath in a second particular manner.

7. The respiratory drug delivery apparatus according to claim 6, wherein the one or more feedback devices include a plurality of LEDs and wherein the first indication, the second indication, the third indication, the fourth indication and the fifth indication each comprise causing an associated one of the LEDs to emit light of a certain color.

8. The respiratory drug delivery apparatus according to claim 3, wherein the feedback and compliance device includes an outer housing, wherein the outer housing including a top portion located above the opening, a bottom portion located below the opening, a front side and a rear side, the outlet extending outwardly from the front side, wherein the force sensing device is provided in the housing in the bottom portion.

9. The respiratory drug delivery apparatus according to claim 8, wherein the bottom portion includes a channel extending completely therethrough from the rear side to the front side, the channel being structured to allow fluid flow through the housing, and wherein the flow sensor is positioned in the bottom portion adjacent to the channel.

10. The respiratory drug delivery apparatus according to claim 8, wherein the one or more feedback devices include a plurality of LEDs provided in the top portion on the front side of the housing.

11. The respiratory drug delivery apparatus according to claim 1, wherein the feedback and compliance device includes a housing defining the opening, the housing including a top portion located above the opening, a bottom portion located below the opening, a front side and a rear side, the outlet extending outwardly from the front side, and wherein the infra-red sensors are provided in the top portion on the front side.

12. The respiratory drug delivery apparatus according to claim 1, wherein the one or more feedback devices include a plurality of LEDs, and wherein the processing unit is programmed to cause selected ones of the LEDs to emit light of a certain color based on an output of at least one of the one or more sensors, the feedback information comprising the light of a certain color.

13. The respiratory drug delivery apparatus according to claim 1, wherein the one or more feedback devices include a speaker, and wherein the processing unit is programmed to cause the speaker to provide the audible instructions relating to proper use of the respiratory drug delivery apparatus based on an output of at least one of the one or more sensors.

14. The respiratory drug delivery apparatus according to claim 1, wherein the feedback and compliance device comprises an infra-red sensor for sensing opening of the exhalation valve.

15. The respiratory drug delivery apparatus according to claim 1, wherein the one or more sensors include one or more microphones to detect sounds indicative of inhalation and/or actuation of the medication delivery device.

16. A method of encouraging proper use of a respiratory drug delivery apparatus including a medication storage and delivery device having an outlet, and a valved holding chamber including a main chamber, an adapter coupled to the main chamber, and an exhalation valve, wherein the medication storage and delivery device is a metered dose inhaler having a canister received in a boot, the outlet being part of the boot, the method comprising:

providing a feedback and compliance device, the feedback and compliance device including one or more sensors, individual ones of the one or more sensors being structured to sense a parameter relating to use of the respiratory drug delivery apparatus without modifying or interfering with a flow of medication introduced by actuation of the medication storage and delivery device; wherein the one or more sensors include an infra-red sensor for sensing air temperature moving through the exhalation valve of the valved holding chamber, and an infra-red sensor for sensing a position of the respiratory drug delivery apparatus relative to a face of a patient, the valved holding chamber coupled to the feedback and compliance device;

removably attaching the feedback and compliance device to the adapter via a connector extending from the feedback and compliance device, the connector being structured to be received and held within a slot provided in the adapter;

coupling the metered dose inhaler to the feedback and compliance device by inserting the outlet through an opening provided in the feedback and compliance device;

receiving and holding the outlet of the boot of the metered dose inhaler by the adaptor, wherein the feedback and compliance device is held and positioned between a portion of the metered dose inhaler and the adapter; and providing feedback information to a patient, in the form of audible instructions, regarding use of the respiratory drug delivery apparatus based on an output of at least one of the one or more sensors.

17. The method according to claim 16, wherein the feedback information is visual, or tactile, or a combination thereof.

18. The method according to claim 16, wherein the providing feedback information comprises: (i) determining in the feedback and compliance device that the medication storage and delivery device has been inserted into the feedback and compliance device and in response thereto providing an instruction to shake the medication storage and delivery device, (ii) determining in the feedback and compliance device that the medication storage and delivery device has been shaken and in response thereto providing an instruction to actuate the medication storage and delivery device, (iii) determining in the feedback and compliance device that the medication storage and delivery device has been actuated and in response thereto providing an instruction to inhale in a first particular manner, and (iv) determining in the feedback and compliance device that inhalation in the first particular manner has been completed and in response thereto providing instruction instructing the patient to hold his or her breath in a second particular manner.

19. The method according to claim 16, wherein the providing feedback information comprises: (i) determining in the feedback and compliance device that the medication storage and delivery device has been inserted into the feedback and compliance device and in response thereto providing a first indication indicating that the medication storage and delivery device has been properly inserted into the feedback and compliance device, (ii) determining in the feedback and compliance device that medication storage and delivery device has been shaken and in response thereto providing a second indication indicating that the medication storage and delivery device has been properly shaken, (iii) determining in the feedback and compliance device that the medication storage and delivery device has been actuated and in response thereto providing a third indication indicating that the medication storage and delivery device has been properly actuated, (iv) determining in the feedback and compliance device that inhalation in a first particular manner has been completed and in response thereto providing a fourth indication indicating that inhalation has been properly performed, and (v) determining in the feedback and compliance device that the patient has held his or her breath in a second particular manner and in response thereto providing a fifth indication indicating that breath hold has been properly performed.

20. The method according to claim 19, wherein the first indication, the second indication, the third indication, the fourth indication and the fifth indication each comprise a visual indication.

21. The method according to claim 16, wherein the one or more sensors include one or more microphones to detect sounds indicative of inhalation and/or actuation of the medication delivery device.

22. A feedback and compliance device for use with a respiratory medication storage and delivery device, comprising:

a housing having an opening, the opening being structured to receive an outlet of the medication storage and delivery device, the medication storage and delivery device being a metered dose inhaler having a canister received in a boot, the outlet being part of the boot;

one or more sensors, individual ones of the one or more sensors being structured to sense a parameter relating to use of the medication storage and delivery device without modifying or interfering with a flow of medication introduced by actuation of the medication storage and delivery device; wherein the one or more sensors include an infra-red sensor for sensing air temperature moving through an exhalation valve of a valved holding chamber, and an infra-red sensor for sensing a position of the respiratory drug delivery apparatus relative to a face of a patient, the valved holding chamber coupled to the feedback and compliance device, wherein the valved holding chamber includes a main chamber, an adapter coupled to the main chamber, and wherein:

the feedback and compliance device structured to be removably attached to the adapter via a connector extending from the feedback and compliance device, the connector being structured to be received and held within a slot provided in the adapter;

the adapter receiving and holding the outlet of the boot of the metered dose inhaler, wherein the feedback and compliance device is held and positioned between a portion of the metered dose inhaler and the adapter;

one or more feedback devices; and a processing unit programmed to cause the one or more feedback devices to provide feedback information to a patient regarding use of the medication storage and delivery device based on an output of at least one of the one or more sensors, wherein the processing unit is programmed to cause the one or more feedback devices to provide feedback information in the form of audible instructions.

23. The feedback and compliance device according to claim 22, wherein the one or more sensors include: (i) a motion sensing device for sensing shaking of the medication storage and delivery device, (ii) a flow sensor for sensing inhalation by the patient, and (iii) a force sensing device for sensing actuation of the medication storage and delivery device.

24. The feedback and compliance device according to claim 23, wherein the processing unit is programmed to cause the one or more feedback devices to provide feedback information in the form of: (i) an instruction to shake the medication storage and delivery device in response to determining that the medication storage and delivery device has been inserted into the feedback and compliance device, (ii) an instruction to actuate the medication storage and delivery device in response to determining that the medication storage and delivery device has been shaken, (iii) an instruction to inhale in a first particular manner in response to determining that the medication storage and delivery device has been actuated, and (iv) an instruction instructing the patient to hold his or her breath in a second particular manner in response to determining that inhalation in the first particular manner has been completed.

25. The feedback and compliance device according to claim 23, wherein the processing unit is programmed to cause the one or more feedback devices to provide feedback information in the form of: (i) a first indication indicating that the medication storage and delivery device has been properly inserted into the feedback and compliance device in response to determining that the medication storage and delivery device has been inserted into the feedback and compliance device, (ii) a second indication indicating that the medication storage and delivery device has been properly shaken in response to determining that the medication storage and delivery device has been shaken, (iii) a third indication indicating that the medication storage and delivery device has been properly actuated in response to determining that the medication storage and delivery device has been actuated, (iv) a fourth indication indicating that inhalation has been properly performed in response to determining that inhalation in a first particular manner has been completed, and (v) a fifth indication indicating that breath hold has been properly performed in response to determining that the patient has held his or her breath in a second particular manner.

26. The feedback and compliance device according to claim 25, wherein the one or more feedback devices include a plurality of LEDs and wherein the first indication, the second indication, the third indication, the fourth indication and the fifth indication each comprise causing an associated one of the LEDs to emit light of a certain color.

27. The feedback and compliance device according to claim 23, wherein the feedback and compliance device includes a housing defining the opening, the housing including a top portion located above the opening, a bottom portion located below the opening, a front side and a rear side, the outlet extending outwardly from the front side, wherein the force sensing device is provided in the housing in the bottom portion.

28. The feedback and compliance device according to claim 27, wherein the bottom portion includes a channel extending completely therethrough from the rear side to the front side, the channel being structured to allow fluid flow through the housing, and wherein the flow sensor is positioned in the bottom portion adjacent to the channel.

29. The feedback and compliance device according to claim 22, comprising an infra-red sensor for sensing opening of the exhalation valve.

30. The feedback and compliance device according to claim 22, wherein the feedback and compliance device includes a housing defining the opening, the housing including a top portion located above the opening, a bottom portion located below the opening, a front side and a rear side, the outlet extending outwardly from the front side, and wherein the infra-red sensors are provided in the top portion on the front side.

31. The feedback and compliance device according to claim 22, wherein the one or more feedback devices include a plurality of LEDs, and wherein the processing unit is programmed to cause selected ones of the LEDs to emit light of a certain color based on an output of at least one of the one or more sensors, the feedback information comprising the light of a certain color.

32. The feedback and compliance device according to claim 22, wherein the one or more feedback devices include a speaker, and wherein the processing unit is programmed to cause the speaker to provide the audible instructions relating to proper use of the respiratory drug delivery apparatus based on an output of at least one of the one or more sensors.

33. The feedback and compliance device according to 22, wherein the one or more sensors include one or more microphones to detect sounds indicative of inhalation and/or actuation of the medication delivery device.

* * * * *